United States Patent [19]

Kulagowski et al.

[11] Patent Number: 5,420,155
[45] Date of Patent: May 30, 1995

[54] TETRAMIC ACID DERIVATIVES

[75] Inventors: Janusz J. Kulagowski, Bishops Stortford; Paul D. Leeson, Cambridge; Ian M. Mawer, Bishops Stortford, all of England

[73] Assignee: Merck Sharp & Dohme Ltd., Hoddesdon, England

[21] Appl. No.: 60,584

[22] Filed: May 10, 1993

[30] Foreign Application Priority Data

May 15, 1992 [GB] United Kingdom ............. 9210393

[51] Int. Cl.$^6$ ............ C07D 207/273; A61K 31/40
[52] U.S. Cl. .................. 514/425; 514/235.5; 514/343; 514/414; 548/544; 548/511; 548/469; 548/454; 546/281; 544/82; 544/124; 544/131; 544/141
[58] Field of Search ........... 548/544, 511, 469, 454; 514/425, 343, 414, 235.5; 546/281; 544/82, 124, 131, 141

[56] References Cited

U.S. PATENT DOCUMENTS 3,931,207  1/1976  Weinstock ............. 548/195
3,984,559  10/1976  Weinstock ............. 514/343

OTHER PUBLICATIONS

CA86(9):55276a Compositions ... Arthritis, Weinstock p. 424, 1977.

Primary Examiner—Mary C. Lee
Assistant Examiner—Joseph K. McKane
Attorney, Agent, or Firm—Robert J. North; Joseph F. DiPrima

[57] ABSTRACT

A class of 4-hydroxy-2(1H)-pyrrolone derivatives, substituted at the 3-position by an optionally substituted aryl substituent, are selective non-competitive antagonists of NMDA receptors and/or are antagonists of AMPA receptors, and are therefore of utility in the treatment of conditions, such as neurodegenerative disorders, convulsions or schizophrenia, which require the administration of an NMDA and/or AMPA receptor antagonist.

9 Claims, No Drawings

TETRAMIC ACID DERIVATIVES

This invention relates to a family of tetramic acid derivatives. More particularly, the invention relates to a class of 4-hydroxy-2(1H)-pyrrolones which are substituted in the 3-position by an optionally substituted aryl substituent. These compounds are selective non-competitive antagonists of N-methyl-D-aspartate (NMDA) receptors. More particularly, the class of compounds provided by the present invention are ligands for the strychnine-insensitive glycine modulatory site of the NMDA receptor and are therefore useful in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by exogenous and endogenous NMDA receptor agonists and neurotoxins, including environmental neurotoxins.

By virtue of their NMDA receptor antagonist properties, the compounds according to the present invention are also useful as anticonvulsant and antiemetic agents, as well as being of value in the prevention or reduction of dependence on dependence-inducing agents such as narcotics.

NMDA receptor antagonists have recently been shown to possess analgesic (see, for example, Dickenson and Aydar, Neuroscience Lett., 1991, 121, 263; Murray et al., Pain, 1991, 44, 179; and Woolf and Thompson, Pain, 1991, 44, 293) and anxiolytic (see, for example, U.S. Pat. No. 5,145,866; and Kehne et al., Eur. J. Pharmacol., 1991, 193., 283) effects, and the compounds of the present invention may accordingly be useful in the management of pain and anxiety.

Compounds possessing functional antagonist properties for the NMDA receptor complex are stated in WO-A-91/19493 to be effective in the treatment of mood disorders, including major depression, bipolar disorder, dysthymia and seasonal affective disorder(cf. also Trullas and Skolnick, Eur. J. Pharmacol., 1990, 185, 1). The compounds of the present invention may consequently be of benefit in the treatment and/or prevention of such disorders.

The association of NMDA receptor antagonists with regulation of the dopaminergic system has recently been reported (see, for example, Werling et al., J. Pharmacol. Exp. Ther., 1990, 255, 40; Graham et al., Life Sciences, 1990, 47, PL-41; Hutson et al., Br. J. Pharmacol., 1991, 103, 2037; and Turski et al., Nature (London), 1991, 349, 414). This suggests that the compounds of the present invention may thus be of assistance in the prevention and/or treatment of disorders of the dopaminergic system such as schizophrenia and Parkinson's disease.

It has also been reported recently (see Lauritzen et al., Journal of Cerebral Blood Flow and Metabolism, 1991, vol. 11, suppl. 2, Abstract XV-4) that NMDA receptor antagonists block cortical spreading depression (CSD), which may thus be of clinical importance since CSD is a possible mechanism of migraine. The class of substituted 2-amino-4-phosphonomethylalkyl-3-ene carboxylic acids and esters described in EP-A-0420806, which are stated to be selective NMDA antagonists, are alleged thereby to be of potential utility in the treatment of inter alia migraine.

Excitatory amino acid receptor antagonists, including inter alia antagonists of NMDA receptors, are alleged in EP-A-0432994 to be of use in suppressing emesis.

Recent reports in the literature have also suggested a link between the neurotoxicity of certain viruses and the deleterious effects of these viruses on an organism caused by the potentiation of neurotransmission via excitatory amino acid receptors. By virtue of their activity as antagonists of NMDA receptors, therefore, the compounds of the present invention may be effective in controlling the manifestations of neuroviral diseases such as measles, rabies, tetanus (cf. Bagetta et al., Br. J. Pharmacol., 1990, 101, 776) and AIDS (cf. Lipton et al., Society for Neuroscience Abstracts, 1990, 16, 128.11).

NMDA antagonists have, moreover, been shown to have an effect on the neuroendocrine system (see, for example, van den Pol et al., Science, 1990, 250, 1276; and Urbanski, Endocrinology, 1990, 127 2223), and the compounds of this invention may therefore also be effective in the control of seasonal breeding in mammals.

In addition, certain compounds of the invention are antagonists of 2-amino-3-hydroxy-5-methyl-4-isoxazolepropionic acid (AMPA) receptors, also known as quisqualate receptors. An excitatory amino acid projection from the prefrontal cortex to the nucleus accumbens (a particular region of the forebrain possessing dopamine-sensitive neurones) is well known to exist (see, for example, J. Neurochem., 1985, 45, 477). It is also well known that dopaminergic transmission in the striatum is modulated by glutamate (see, for example, Neurochem. Int., 1983, 5, 479), as also is the hyperactivity associated with presynaptic stimulation of the dopamine system by AMPA in the nucleus accumbens (cf. Life Sci., 1981, 28, 1597). Compounds which are antagonists of AMPA receptors are therefore of value as neuroleptic agents.

In U.S. Pat. Nos. 3,931,207 and 3,984,559 there is described a family of tetramic acid analogues of pulvinic acid which are stated to have anti-arthritic activity and, in addition, anti-bacterial activity. There is no suggestion in either of these publications, however, that the compounds described therein might be of assistance in solving the problem of providing an effective agent for the treatment and/or prevention of conditions requiring the administration of an antagonist of NMDA and/or AMPA receptors.

The present invention accordingly provides a compound of formula I, or a salt or prodrug thereof:

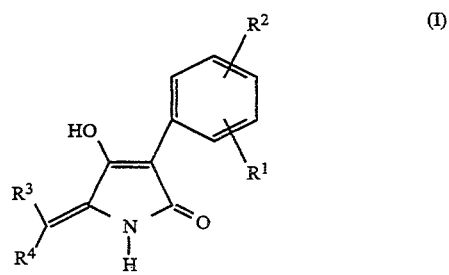

wherein
R$^1$ and R$^2$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; or R$^1$ and R$^2$ together represent the residue of a carbocyclic or heterocyclic ring;

R$^3$ and R$^4$ independently represent hydrogen, hydrocarbon, a heterocyclic group, trifluoromethyl, —OR$^c$, —SR$^c$, —SOR$^a$, —SO$_2$R$^a$, —SO$_2$NR$^a$R$^b$, —COR$^a$, —CO$_2$R$^a$ or —CONR$^a$R$^b$, provided that R$^3$ does not represent C$_{2-5}$ alkoxycarbonyl when R$^4$ represents an optionally substituted phenyl group;

R$^a$ and R$^b$ independently represent hydrogen, hydrocarbon or a heterocyclic group; and R$^c$ represents hydrocarbon or a heterocyclic group.

The present invention also provides the use of a compound of formula I as defined above or a pharmaceutically acceptable salt thereof or a prodrug thereof for the manufacture of a medicament for the treatment and/or prevention of conditions, in particular neurodegenerative disorders, which require the administration of a selective non-competitive antagonist of NMDA receptors.

The present invention further provides the use of a compound of formula I as defined above or a pharmaceutically acceptable salt thereof or a prodrug thereof for the manufacture of a medicament for the treatment and/or prevention of conditions, such as schizophrenia, which require the administration of an antagonist of AMPA receptors.

In a further aspect, the invention provides a pharmaceutical composition comprising a compound of formula I as defined above or a pharmaceutically acceptable salt thereof or a prodrug thereof in association with one or more pharmaceutically acceptable carriers and/or excipients.

In a still further aspect, the invention provides a compound of formula I as defined above or a pharmaceutically acceptable salt thereof or a prodrug thereof for use in therapy.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl (C$_{1-6}$) alkyl, aryl, aryl(C$_{1-6}$)alkyl, aryl(C$_{2-6}$)alkenyl and aryl(C$_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, n-butyl and t-butyl.

Suitable alkenyl groups include straight-chained and branched alkenyl groups containing from 2 to 6 carbon atoms. Typical examples include vinyl, allyl and methylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl(C$_{1-6}$)alkyl group is benzyl.

A particular aryl(C$_{2-6}$)alkenyl group is phenylethenyl.

A particular aryl(C$_{2-6}$)alkynyl group is phenylethynyl.

Suitable heterocycloalkyl groups include piperidyl, piperazinyl and morpholinyl groups.

A particular heterocycloalkyl(C$_{1-6}$)alkyl group is morpholinylethyl.

Suitable heteroaryl groups include pyridyl, quinolyl, isoquinolyl, pyridazinyl, pyrimidinyl, pyrazinyl, pyrrolyl, indolyl, pyranyl, furyl, benzofuryl, thienyl, benzthienyl, imidazolyl, oxadiazolyl and thiadiazolyl groups. Particular heteroaryl groups are pyridyl, pyrrolyl, indolyl, furyl, benzofuryl, thienyl, benzthienyl and oxadiazolyl.

Particular heteroaryl(C$_{1-6}$)alkyl groups include pyridylmethyl, pyrrolylmethyl, indolylmethyl, furylmethyl and thienylmethyl.

Where R$^1$ and R$^2$ together represent the residue of a carbocyclic or heterocyclic ring, the ring may be saturated or unsaturated. The ring may suitably be a 4-to 9-membered ring, but will preferably be a 5- or 6-membered ring. Where R$^1$ and R$^2$ together represent the residue of a heterocyclic ring, this ring may contain up to four heteroatoms selected from oxygen, nitrogen and sulphur. Suitable carbocyclic rings of which R$^1$ and R$^2$ together represent the residue include cyclohexane, cyclohexene, cyclohexadiene and benzene rings. Suitable heterocyclic rings of which R$^1$ and R$^2$ together represent the residue include dioxolane, dioxane, pyridine, furan, thiophene, pyrrole, thiazole and thiadiazole rings.

The hydrocarbon and heterocyclic groups, as well as the carbocyclic or heterocyclic ring completed by R$^1$ and R$^2$, may in turn be optionally substituted by one or more groups selected from C$_{1-6}$ alkyl, adamantyl, phenyl, halogen, C$_{1-6}$ haloalkyl, morpholinyl(C$_{1-6}$)alkyl, trifluoromethyl, hydroxy, C$_{1-6}$alkoxy, C$_{1-6}$ alkoxy(C$_{1-6}$)alkyl, C$_{1-6}$ alkoxy(C$_{1-6}$)alkoxy, aryloxy, keto, C$_{1-3}$ alkylenedioxy, nitro,-cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, C$_{2-6}$alkylcarbonyl, arylcarbonyl, C$_{1-6}$ alkylthio, C$_{1-6}$ alkylsulphinyl, C$_{1-6}$ alkylsulphonyl, amino, mono- or di(C$_{1-6}$)alkylamino, C$_{2-6}$ alkylcarbonylamino and C$_{2-6}$ alkoxycarbonylamino.

The term "halogen" as used herein includes fluorine, chlorine, bromine and iodine, especially chlorine.

Suitable values for the substituents R$^1$ and R2include C$_{1-6}$ alkyl, aryl, aryl(C$_{1-6}$)alkyl, aryl(C$_{2-6}$)alkenyl, aryl(C$_{2-6}$)alkynyl, heteroaryl(C$_{1-6}$)alkyl, C$_{1-6}$ alkoxy, C$_{2-6}$ alkenyloxy, aryloxy, aryl(C$_{1-6}$)alkoxy, heteroaryloxy, arylthio, arylsulphonyl, arylamino, aryl(C$_{1-6}$)alkylamino, di(C$_{1-6}$)alkylamino, arylcarbonylamino, arylcarbonyl or heteroarylcarbonyl, any of which groups may be optionally substituted; and hydrogen, halogen, trifluoromethyl or nitro. Examples of optional substituents on the groups R$^1$ and/or R$^2$ include C$_{1-6}$ alkyl, morpholinyl (C$_{1-6}$) alkyl, hydroxy, C$_{1-6}$ alkoxy, C$_{1-6}$ alkoxy(C$_{1-6}$)alkyl, C$_{1-6}$ alkoxy(C$_{1-6}$)alkoxy, C$_{1-6}$ alkylthio and di(C$_{1-6}$) alkylamino.

Particular values for the substituents R¹ and R² include hydrogen, methyl, phenyl, benzyl, methoxymethyl-benzyl, morpholinylethyl-benzyl, hydroxybenzyl, methoxybenzyl, methoxymethoxy-benzyl, methylthiobenzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methyl-phenoxy, methoxyphenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

Suitably, at least one of R¹ and R² represents hydrogen.

Where R¹ and R² together represent the residue of a carbocyclic or heterocyclic ring, this may be, in particular, a dioxolane or optionally substituted benzene ring.

Suitable values for the substituents R³ and R⁴ include hydrogen; and $C_{1-6}$ alkyl, $C_{3-7}$ cycloalkyl, aryl or $C_{1-6}$ alkoxy, any of which groups may be optionally substituted, most especially by one or more halogen atoms.

Particular values for the substituents R³ and R⁴ include hydrogen, ethyl, n-propyl, n-butyl, cyclopropyl and phenyl.

Preferably, at least one of R³ and R⁴ represents hydrogen. In an especial embodiment, R³ is hydrogen and R⁴ is other than hydrogen.

For use in medicine, the salts of the compounds of formula I will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formula I above include alkali metal salts, e.g. lithium, sodium or potassium salts; alkaline earth metal salts, e.g. calcium or magnesium salts; and salts formed with suitable organic ligands, e.g. quaternary ammonium salts. Where appropriate, acid addition salts may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

One sub-class of compounds according to the invention is represented by the compounds of formula IIA and salts and prodrugs thereof:

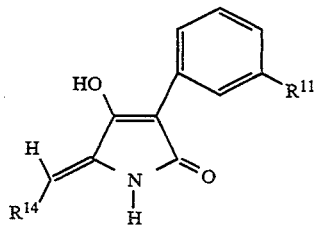

(IIA)

wherein

R¹¹ represents $C_{1-6}$ alkyl, $C_{2-6}$ alkenyl, $C_{2-6}$ alkynyl, aryl, aryl($C_{1-6}$)alkyl, aryl($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl($C_{1-6}$)alkylamino, di($C_{1-6}$)alkylamino, arylcarbonylamino, arylcarbonyl, heteroarylcarbonyl or $C_{2-7}$ alkoxycarbonyl, any of which groups may be optionally substituted; or hydrogen, halogen, cyano, trifluoromethyl, nitro, hydroxy, amino or carboxy; and R¹⁴ represents hydrogen, $C_{1-6}$ alkyl, halo($C_{1-6}$)alkyl, $C_{3-7}$ cycloalkyl, aryl, haloaryl or $C_{1-6}$ alkoxy.

Examples of optional substituents on the group R¹¹ include $C_{1-6}$ alkyl, morpholinyl($C_{1-6}$)alkyl, hydroxy, $C_{1-6}$ alkoxy, $C_{1-6}$ alkoxy($C_{1-6}$)alkyl, $C_{1-6}$ alkoxy($C_{1-6}$)alkoxy, $C_{1-6}$ alkylthio and di($C_{1-6}$)alkylamino.

Particular values of R¹¹ with respect to formula IIA include hydrogen, methyl, phenyl, benzyl, methoxymethyl-benzyl, morphol inylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methylphenoxy, methoxy-phenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl; especially hydrogen, methyl-allyloxy or phenoxy.

Particular values of R¹⁴ include ethyl, n-propyl, n-butyl, cyclopropyl and phenyl.

Specific compounds within the scope of the present invention include:

(Z)-5-(1'-cyclopropylmethylidene)-4-hydroxy-3-phenyl -2(1H)-pyrrolone;

(Z)-4-hydroxy-3-phenyl-5-(1'-phenylmethylidene)-2(1H)-pyrrolone;

(Z)-4-hydroxy-3-phenyl-5-(1'-propylmethylidene)-2(1H)-pyrrolone;

(Z)-5-(1'-ethylmethylidene)-4-hydroxy-3-(3-phenoxyphenyl)-2(1H)-pyrrolone;

(Z)-5-(1'-ethylmethylidene)-4-hydroxy-3-phenyl-2(1H)-pyrrolone;

(Z)-5-(1'-ethylmethylidene)-4-hydroxy-3-(2-methyl-2-propenyloxy)phenyl-2(1H)-pyrrolone; and salts and prodrugs thereof.

The pharmaceutical compositions of this invention are preferably in unit dosage forms such as tablets, pills, capsules, powders, granules, sterile solutions or suspensions, or suppositories, for oral, intravenous, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical. vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of conditions requiring the administration of an NMDA antagonist, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day. In a particular embodiment, the compounds may be conveniently administered by intravenous infusion.

The compounds of formula I above may be prepared by a process which comprises cyclising a compound of formula III:

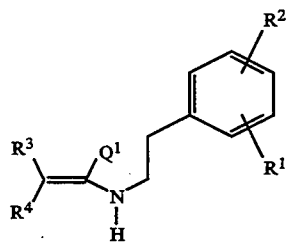

(III)

wherein $R^1$, $R^2$, $R^3$ and $R^4$ are as defined above; and $Q^1$ represents a reactive carboxylate moiety.

The reaction is conveniently carried out in the presence of a base such as potassium hexamethyldisilazide, typically at room temperature in a suitable solvent, e.g. tetrahydrofuran/toluene.

Suitable values for the reactive carboxylate moiety $Q^1$ include esters, for example $C_{1-4}$ alkyl esters; acid anhydrides, for example mixed anhydrides with $C_{1-4}$ alkanoic acids; acid halides, for example acid chlorides; orthoesters; and primary, secondary and tertiary amides.

Preferably, the group $Q_1$ represents methoxycarbonyl or ethoxycarbonyl.

The intermediates of formula III above may conveniently be prepared by Horner-Emmons reaction between a carbonyl compound of formula IV and a phosphonate derivative of formula V:

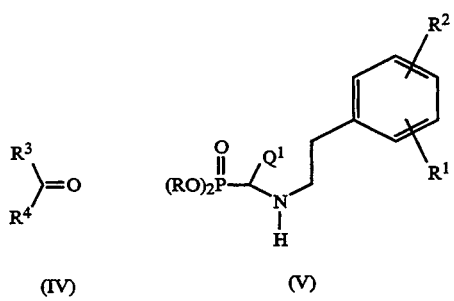

(IV)       (V)

wherein $R^1$, $R^2$, $R^3$, $R^4$ and $Q^1$ are as defined above; and R is $C_{1-4}$ alkyl, especially methyl.

The reaction is conveniently effected by treating a solution of the phosphonate V, ideally at a temperature below $-60°$ C., with a strong base such as potassium t-butoxide, and subsequently adding a solution of the carbonyl compound IV before allowing the resulting reaction mixture to warm to room temperature. A typical solvent for use in connection with this reaction is dichloromethane.

The intermediates of formula V above wherein $Q^1$ is methoxycarbonyl and R is methyl may conveniently be prepared from methyl 2-benzyloxycarbonylamino-2-(dimethoxyphosphinyl)acetate by catalytic hydrogenation over palladium hydroxide followed by condensation of the resulting α-amino ester with a carboxylic acid derivative of formula VI:

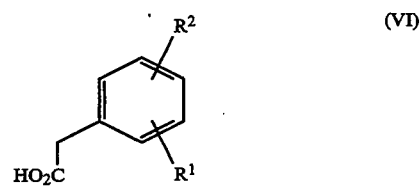

(VI)

wherein $R^1$ and $R^2$ are as defined above; advantageously in the presence of 1,3-dicyclohexylcarbodiimide. The intermediates of formula V wherein $Q^1$ is other than methoxycarbonyl and/or R is other than methyl may be prepared analogously.

The starting compound methyl 2-benzyloxycarbonylamino-2-(dimethoxyphosphinyl)acetate can be prepared as described in *Synthesis*, 1984, 53.

Where they are not commercially available, the starting materials of formulae IV and VI above may be prepared by methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently and selectively block responses to NMDA and/or AMPA in a brain slice from rat cortex, and inhibit the binding of agonists and antagonists to the strychnine-insensitive site present on the NMDA receptor and/or AMPA binding to rat forebrain membranes.

Cortical Slice Studies

The effects of compounds of the invention on responses to NMDA and AMPA were assessed using the rat cortical slice as described by Wong et al., i Proc. Natl. Acad. Sci. USA, 1986, 83, 7104. The apparent equilibrium constant ($K_b$) was calculated from the right-hand shift in the NMDA or AMPA concentration-response curves produced by the compound under test. Of those compounds of the accompanying Examples which were tested, all were found to possess $K_b$ values in response to NMDA of below 200 $\mu$M.

Binding Studies

The ability of test compounds to displace $^3$H-L-689,560 (trans-2-carboxy-5,7-dichloro-4-phenyl-aminocarbonylamino-1,2,3,4-tetrahydroquinoline) binding to the strychnine-insensitive site present on the NMDA receptor of rat forebrain membranes was determined by the method of Grimwood et al., *Proceedings of The British Pharmacological Society.*, Jul. 1991, Abstract C78. The concentration of the compounds of the accompanying Examples required to displace 50% of the specific binding (IC$_{50}$) is below 50 $\mu$M in each case.

EXAMPLE 1

Step 1: 2-Amino-2-(dimethoxyphosphinyl)acetate

A solution of methyl 2-benzyloxycarbonylamino-2-(dimethoxyphosphinyl)acetate [Schmidt et al, Synthesis, 1984, 53], (15g, 45.3mmol) in methanol (150ml) was hydrogenated over 10% palladium hydroxide on carbon (1g) at 50 psi for 2 hours. Removal of the catalyst and evaporation of the filtrate yielded the product as an oil (8g, 100%); $\delta_H$ (DMSO-d$_6$) 1.95 (2H, br s, NH$_2$), 3.81–3.86 (9H, m, P(O)(OMe)$_2$, CO$_2$Me), 3.98 (1H, d, J 21.3 Hz, CHCO$_2$Me).

Step 2: Methyl 2-dimethoxyphosphinyl-2-(phenyl acetylamino)acetate

To a solution of the foregoing amine (8 g, 45.3 mmol) in dichloromethane (40 ml) at −10° C. was added a solution of phenylacetic acid (6.16 g, 45.3 mmol) in dichloromethane (60 ml), followed by dicyclohexylcarbodiimide (10.3 g, 50 mmol) and the reaction stirred at room temperature for 48 hours. The precipitate was removed by filtration and the filtrate washed with 1M potassium hydrogen sulphate (60 ml), saturated sodium carbonate (60ml), dried (MgSO$_4$) and evaporated to yield the product as a solid (12 g); $\delta_H$(CDCl$_3$) 3.64 (2H, s, CH$_2$Ph), 3.70 (6H, dd, J 57.7, 14.4 Hz, P(O)(OMe)$_2$), 3.79 (3H, s, CO$_2$Me), 5.22 (1H, dd, J 22.0, 8.9 Hz, CHCO$_2$Me), 6.29 (1H, d, J 4.3 Hz, NH), 7.26–7.38 (5H, m, ArH).

Step 3: Methyl (Z)-3-cycopropyl-2-(phenyl acetylamino)prop-2-enoate

To a suspension of potassium tert-butoxide (317 mg, 6.4 mmol) in dry dichloromethane (5 ml) at −70° C. was added a solution of the foregoing phosphonate (2 g, 6.4 mmol) in dichloromethane (20 ml) keeping the temperature below −60° C. The reaction was stirred for 10 minutes before addition of a solution of cyclopropylcarboxaldehyde (576 $\mu$l, 7.6 mmol) in dichloromethane (5 ml). The reaction was warmed to room temperature and stirred for 2 hours. The solvent was evaporated and the residue partitioned between ethyl acetate (100 ml) and water (30 ml). The organic phase was washed with saturated ammonium chloride (30ml), dried (MgSO$_4$) and evaporated. The residue was chromatographed on silica (eluting with 35% ethyl acetate/60°–80° petrol) to remove trace amounts of the (E)-isomer before yielding the title compound as a solid (1 g, 64%); $\delta_H$ (CDCl$_3$) 0.63–0.67 (2H, m, cPr methylene), 0.96.–1.01 (2H, m, cPr methylene), 1.45–1.52 (1H, m, cPr methine), 3.70 (3H, s, CO$_2$Me), 3.72 (2H, s, CH$_2$Ph), 6.11 (1H, d, J 10.8 Hz, 3–CH), 7.29–7.40 (5H, m, ArH).

Step 4: (Z)-5-(1′-Cyclopropylmethylidene)-4-hydroxy-3-phenyl-2(1H)-pyrrolone

To a solution of the above amide (700 mgs, 2.7 mmol) in dry tetrahydrofuran (20 ml) was added a solution of potassium hexamethyldisilazide in toluene (0.5M, 13 ml, 6.5 mmol) and the reaction stirred at room temperature for 1 hour. The reaction was quenched by addition of methanol (5 ml)and the solvent evaporated to dryness. The residue was dissolved in the minimum amount of methanol and acidified with trifluoroacetic acid. The resultant solution was evaporated and the residue recrystallised from ethyl acetate/60°–80° C. petrol to yield the product as a white solid; m.p. 167°–170° C. (Found: C, 73.77; H, 6.20; N, 6.49; C$_{14}$H$_{13}$NO$_2$, 0.2H$_2$O requires C, 73.41; H, 5.81; N, 6.12%); $\delta_H$ (DMSO-d$_6$) 0.52–0.55 (2H, m, cPr methylene), 0.91–0.94 (2H, m, cPr methylene), 1.80–1.88 (1H, m, cPr methine), 5.13 (1H, d, J 10.5 Hz, C-CH-cPr), 7.18 (1H, t, J 7.3 Hz, ArH), 7.33 (2H, J 7.8 Hz, ArH), 7.91 (2H, d, J 7.2 Hz, ArH), 9.68 (1H, s, NH), 10.72 (1H, s, OH); m/z 227 (M+).

The following were prepared in analogous manner.

EXAMPLE 2

(Z)-4-Hydroxy-3-phenyl-5-(1'-phenyl)methylidene-2(1H)-pyrrolone m.p. 237°–239° C. (from aqueous methanol) (Found: C, 77.29; H, 4.99; N, 5.27; $C_{17}H_{13}NO_2$ requires C, 77.55; H, 4.98; N, 5.32%); $\delta_H$ (DMSO-$d_6$) 6.51 (1H, s, PhCHC), 7.21–7.30 (2H, m, ArH), 7.36–7.41 (4H, m, ArH), 7.57 (2H, d, J 7.3 Hz, ArH), 7.91 (2H, d, J 7.1 Hz, ArH), 9.69 (1H, s, NH); m/z 263 (M+).

EXAMPLE 3

(Z)-4-Hydroxy-3-phenyl-5-(1'-propyl)methylidene-2(1H)-pyrrolone m.p. 170°–173° C. (from aqueous methanol) (Found: C, 72.01; H, 6.68; N, 6.01; $C_{14}H_{15}NO_2$, 0.2$H_2O$ requires C, 72.20; H, 6.66; N, 6.01%); $\delta_H$(DMSO-$d_6$) 0.92 (3H, t, J 7.3 Hz, $CH_3$), 1.43 (2H, q,-J 7.3, 14.8 Hz, $CH_2CH_3$), 2.22 (2H, q, J 7.3, 14.8 Hz, $CH_2CH_2CH_3$), 5.64 (1H, t, J 7.9 Hz, $CHCH_2$), 7.18 (1H, t, J 7.3 Hz, ArH), 7.33 (2H, J 7.8 Hz, ArH), 7.91 (2H, d, J 7.2 Hz, ArH), 9.40 (1H, s, NH); m/z 229 (M+).

EXAMPLE 4

(Z)-5-(1'-Ethyl)methylidene-4-hydroxy-3-(3-phenoxy)-phenyl-2-(1H)-pyrrolone m.p. 164°–167° C. (from ethyl acetate/60°–80° petrol) (Found: C, 73.30; H, 5.55; N, 4.45; $C_{19}H_{17}NO_3$, 0.15 $H_2O$ requires C, 73.60; H, 5.62; N, 4.52%); $\delta_H$(DMSO-$d_6$) 1.00 (3H, t, J 7.5 Hz, $CH_3$), 2.23 (2H, qt, J 7.5, 7.8 Hz, $CH_2CH_3$), 5.62 (1H, t, J 7.8 Hz, $CHCH_2$), 6.84 (1H, dd, J 7.8, 2.0 Hz, ArH), 7.01 (2H, d, J 8.8 Hz, ArH), 7.11 (1H, t, J 7.5 Hz, ArH), 7.33–7.40 (3H, m, ArH), 7.69 (1H, s, ArH), 7.79 (1H, d, J 7.9 Hz, ArH), 9.49 (1H, s, NH); m/z 307 (M+).

EXAMPLE 5

(Z)-5-(1'-Ethyl)methylidene-4-hydroxy-3-phenyl-2(1H)-pyrrolone m.p. 205°–209° C. (from ethyl acetate/60°–80° petrol) (Found: C, 72.35; H, 5.97; N, 6.48; $C_{13}H_{13}NO_2$ requires: C, 72.54; H, 6.09; N, 6.51%). $\delta_H$(DMSO-$d_6$) 1.02 (3H, t, J 7.5 Hz, $CH_3CH_2$), 2.21–2.29 (2H, m, $CH_3CH_2$), 5.62 (1H, t, J 7.9 Hz,C:$CHCH_2CH_3$), 7.17–7.22 (1H, m, ArH), 7.31–7.36 (2H, m, ArH), 7.89–7.92 (2H, m, ArH), 9.48 (1H, s, NH), 10.87 (1H, br s, OH); m/z 216 (M+).

EXAMPLE 6

(Z)-5-('-Ethyl)methylidene-4-hydroxy-3-(2-methyl-2-propenyloxy)phenyl-2(1H)-pyrrolone m.p. 162°–164° C. (from ethyl acetate/60°–80° petrol) (Found: C, 71.93; H, 6.78; N, 5.04; $C_{17}H_{19}NO_3$ requires C: 71.56; H, 6.71; N, 4.91%) $\delta_H$(DMSO-$d_6$) 1.01 (3H, t, J 7.4 Hz, $CH_3CH_2$), 1.76 (3H, s, $CH_3CCH_2$), 2.20–2.29 (2H, m, $CH_3CH_2CH$), 4.44 (2H, s, $OCH_2C$), 4.95 (1H, s, $CCH_2$), 5.06 (1H, s, $CCH_2$), 5.62 (1H, t, J 7.8 Hz, $CH_2CHC$), 6.79 (1H, dd, J 8.2, 2.5 Hz, ArH), 7.24 (1H, t, J 8.1 Hz, ArH), 7.53–7.58 (2H, m, ArH), 9.48 (1H, s, NH), 10.90 (1H, brs, OH); m/z 285 (M+).

EXAMPLE 7

Tablet Preparation

Tablets containing 1.0, 2.0, 25.0, 26.0, 50.0 and 100.0 mg, respectively of the following compounds are prepared as illustrated below:

(Z)-5-(1'-Cyclopropylmethylidene)-4-hydroxy-3-phenyl-2(1H)-pyrrolone (Z)-4-Hydroxy-3-phenyl-5-(1'-phenyl)methylidene-2(1H)-pyrrolone (Z)-4-Hydroxy-3-phenyl-5-(1'-propyl)methylidene-2(1H)-pyrrolone (Z)-5-(1'-Ethyl)methylidene-4-hydroxy-3-(3-phenoxy)-phenyl-2(1H)-pyrrolone (Z)-5-(1'-Ethyl)methylidene-4-hydroxy-3-phenyl-2(1H)-pyrrolone (Z)-5-(1'-Ethyl)methylidene-4-hydroxy-3-(2-methyl-2-propenyloxy)phenyl-2(1H)-pyrrolone

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A compound of formula I, or a pharmaceutically acceptable salt thereof:

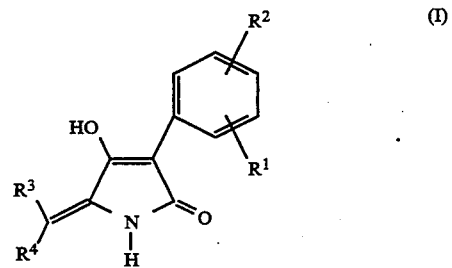

wherein $R^1$ and $R^2$ are independently selected from the group consisting of hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ and —$CONR^aR^b$; or $R^1$ and $R^2$ together represent the residue of a carbocyclic or heterocyclic ring;

$R^3$ and $R^4$ are independently selected from the group consisting of hydrogen, hydrocarbon, a heterocyclic group, trifluoromethyl, —$OR^c$, —$SR^c$, —$SOR^a$, —$SO_2R^a$, —$SO_2NR^aR^b$, —$COR^a$;

$R^a$ and $R^b$ independently represent hydrogen, hydrocarbon or a heterocyclic group; and $R^c$ represents hydrocarbon or a heterocyclic group.

2. A compound according to claim 1 wherein $R^1$ and $R^2$ are independently selected from the group consisting of hydrogen, methyl, phenyl, benzyl, methoxymethylbenzyl, morpholinylethyl-benzyl, hydroxybenzyl, methoxybenzyl, methoxymethoxy-benzyl, methylthio-benzyl, phenylethenyl, phenylethynyl, thienylmethyl, pyrrolylmethyl, indolylmethyl, fluoro, chloro, bromo, iodo, trifluoromethyl, nitro, methoxy, ethoxy, allyloxy, methyl-allyloxy, phenoxy, methyl-phenoxy, methoxyphenoxy, dimethylamino-phenoxy, benzyloxy, furyloxy, thienyloxy, pyridyloxy, phenylthio, phenylsulphonyl, phenylamino, benzylamino, dimethylamino, phenylcarbonylamino, phenylcarbonyl, furylcarbonyl and thienylcarbonyl.

3. A compound according to claim 1 wherein $R^3$ is hydrogen and $R^4$ is other than hydrogen.

4. A compound according to claim 3 wherein $R^4$ is selected from the group consisting of ethyl, n-propyl, n-butyl, cyclopropyl and phenyl.

5. A compound as claimed in claim 1 represented by formula IIA and pharmaceutically acceptable salts thereof:

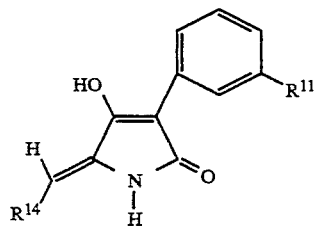

(IIA)

wherein $R^{11}$ is selected from the group consisting of $C_{1-6}$ alkyl, $C_{2-6}$ alkenyl, $C_{2-6}$ alkynyl, aryl, aryl ($C_{1-6}$) alkyl, aryl ($C_{2-6}$)alkenyl, aryl($C_{2-6}$)alkynyl, heteroaryl($C_{1-6}$)alkyl, $C_{1-6}$ alkoxy, $C_{2-6}$ alkenyloxy, aryloxy, aryl($C_{1-6}$)alkoxy, heteroaryloxy, $C_{1-6}$ alkylthio, arylthio, arylsulphonyl, arylamino, aryl ($C_{1-6}$) alkylamino, di($C_{1-6}$)alkylamino, arylcarbonylamino, arylcarbonyl, heteroarylcarbonyl or $C_{2-7}$ alkoxycarbonyl, any of which groups may be optionally substituted; and hydrogen, halogen, cyano, trifluoromethyl, nitro, hydroxy, amino or carboxy; and $R^{14}$ is selected from the group consisting of hydrogen, $C_{1-6}$ alkyl, halo($C_{1-6}$)alkyl, $C_{3-7}$ cycloalkyl, aryl, haloaryl and $C_{1-6}$ alkoxy.

6. A compound selected from:

(Z)-5-(1'-cyclopropylmethylidene)-4-hydroxy-3-phenyl-2(1H)-pyrrolone;

(Z)-4-hydroxy-3-phenyl-5-(1'-phenylmethylidene)-2(1H)-pyrrolone;

(Z)-4-hydroxy-3-phenyl-5-(1'-propylmethylidene)-2(1H)-pyrrolone;

(Z)-5-(1'-ethylmethylidene)-4-hydroxy-3-(3-phenoxyphenyl)-2(1H)-pyrrolone;

(Z)-5-(1'-ethylmethylidene)-4-hydroxy-3-phenyl-2(1H)-pyrrolone;

(Z)-5-(1'-ethylmethylidene)-4-hydroxy-3-(2-methyl-2-propenyloxy)phenyl-2(1H)-pyrrolone; and pharmaceutically acceptable salts thereof.

7. A pharmaceutical composition comprising an effective amount of a compound of formula I as defined in claim 1 or a pharmaceutically acceptable salt thereof in association with one or more pharmaceutically acceptable carriers and/or excipients.

8. A method for the treatment of conditions which require the administration of a selective non-competitive antagonist of NMDA receptors, which comprises administering to a patient in need of such treatment an effective amount of a compound of formula I as defined in claim 1 or a pharmaceutically acceptable salt thereof.

9. A method for the treatment of conditions which require the administration of an antagonist of AMPA receptors, which comprises administering to a patient in need of such treatment an effective amount of a compound of formula I as defined in claim 1 or a pharmaceutically acceptable salt thereof.

* * * * *